United States Patent [19]

Imai et al.

[11] Patent Number: 5,057,438
[45] Date of Patent: Oct. 15, 1991

[54] ELECTROPHORETIC ANTIGEN-ANTIBODY DETERMINATION WITH LAMINATE OF MULTIPLE MEMBRANES

[75] Inventors: Kazumichi Imai; Daizo Tokinaga; Teruaki Kobayashi; Kenji Yasuda; Keiichi Nagai; Satoshi Takahashi, all of Tokyo, Japan

[73] Assignee: Agency of Industrial Science & Technology, Ministry of International Trade & Industry, Tokyo, Japan

[21] Appl. No.: 31,665

[22] Filed: Mar. 30, 1987

[30] Foreign Application Priority Data

Sep. 24, 1986 [JP] Japan .................................. 61-223682
Nov. 7, 1986 [JP] Japan .................................. 61-264056

[51] Int. Cl.$^5$ .......................................... G01N 33/561
[52] U.S. Cl. ..................................... 436/516; 435/723; 435/173; 436/518; 436/809; 436/824
[58] Field of Search ............... 436/516, 514, 518, 528, 436/529, 531, 532, 535, 807, 809, 824, 161, 813; 435/173, 7, 7.23; 422/101

[56] References Cited

U.S. PATENT DOCUMENTS

| | | | |
|---|---|---|---|
| 3,260,413 | 7/1966 | Natelson | 436/170 X |
| 3,930,983 | 1/1975 | Sieber | 436/516 |
| 4,288,425 | 9/1981 | Lee et al. | 436/516 |
| 4,477,575 | 10/1984 | Vogel et al. | 436/177 X |
| 4,628,035 | 12/1986 | Tokinaga et al. | 436/514 X |
| 4,673,657 | 6/1987 | Christian | 436/809 X |

FOREIGN PATENT DOCUMENTS 3429377 3/1985 Fed. Rep. of Germany .

OTHER PUBLICATIONS

"Webster's II New Riverside Dictionary", (Riverside Publishing Co.), 1984, p. 674.

Primary Examiner—David L. Lacey
Assistant Examiner—J. D. Waack
Attorney, Agent, or Firm—Oblon, Spivak, McClelland, Maier & Neustadt

[57] ABSTRACT

Determination of a plurality of species of antibodies or antigens is attained by a method which comprises forming a plurality of different kinds of reaction membranes each having a different species of antibody or antigen on an electrophoretic carrier, superposing these reaction membranes, optionally superposing a filter on the laminate of reaction membranes, inserting the laminate in an electrolyte, adding a plurality of different species of antigens or antibodies corresponding to the plurality of species of antibodies or antigens supported in the aforementioned reaction membranes, electrophoretically moving the added antigens or antibodies through the electrolyte and enabling them to react with the antibodies or antigens supported on the reaction membranes, and measuring the concentrations of either the antigens or antibodies resulting from the reaction or the antibodies or antigens supported in an unreacted form on the reaction membranes.

11 Claims, 3 Drawing Sheets

ELECTROPHORETIC ANTIGEN-ANTIBODY DETERMINATION WITH LAMINATE OF MULTIPLE MEMBRANES

FIELD OF THE INVENTION AND RELATED ART STATEMENT

This invention relates to a method for the determination of antigen or antibody, which is capable of simultaneously and quickly determining concentrations of a plurality of species of antigens or antibodies by means of electrophoresis and is particularly suitable for the measurement of tumor markers, and to an apparatus to be used for working the method.

The measurement of a tumor marker, though not a definitive diagnostic test, is useful as a screening test for cancers because the physical burden imposed thereby on a patient is small as compared with that entailed by a histocytological test or a morphological test and because the specimen used for the measurement is a body fluid such as blood and, therefore, can be readily obtained.

For the screening of cancerous growth by the use of tumor markers to be useful, it must be capable of detecting malignant tumors in a high ratio and also detecting non-cancerous or benign tumors in a high ratio. In other words, the screening must give positive test results for cancerous growth in as high a ratio as possible and, at the same time, give false positive test results in as low a ratio as possible. The various markers heretofore known to the art are not on their own capable of fulfilling these conditions sufficiently. In the circumstances, combination assay in which the measurement is effected by the use of a plurality of such markers in combination for the purpose of improving the diagnostic performance has been developed and the usefulness of this technique has been attracting growing attention.

For the measurement of various tumor markers, various methods of immunoassay have been proposed. However, none of these methods of immunoassay, are capable of effecting the measurements of various tumor markers simultaneously. For such a method of immunoassay to be effectively applied to the aforementioned combination assay, the measurement must be repeated for each of the plurality of tumor markers involved. This is equivalent to saying that as many sample liquids and as many procedure steps are required as the number of different tumor markers.

One of these methods of immunoassay is disclosed in U.S. Pat. No. 4,628,035 and Japanese Patent Public Disclosure No. Sho 60(1985)-57257. This method determines the concentration of an antigen in a sample liquid by immobilizing an antibody on a membranous carrier, applying a potential gradient perpendicularly to the surface of this membrane thereby enabling the antigen in the sample liquid to be moved by means of electrophoresis in the perpendicular direction mentioned above, immobilizing the antigen through an antigen-antibody reaction with the aforementioned immobilized antibody, and further either causing a labeled antibody to move electrophoretically toward and react with the antigen immobilized in the preceding step or immobilizing a labeled antigen on the antibody immobilized in advance on a carrier and not yet altered by reaction, and measuring the concentration of the labeled antigen so immobilized. This method, however, is incapable of simultaneously measuring a plurality of different tumor markers and must repeat the measurement for each of the tumor markers. As an inevitable consequence, the amount of a sample liquid to be used for the measurement becomes large The aforementioned conventional methods, for the reasons given above, have no alternative but to repeat the measurement for each tumor marker where a plurality of different tumor markers are used for the determination. Thus, they have a disadvantage that the measurement requires much time and labor and a large amount of sample liquid.

OBJECT AND SUMMARY OF THE INVENTION

An object of this invention is to provide a method for the determination of antigen and antibody which permits measurement of a plurality of different tumor markers to be simultaneously and quickly carried out by means of electrophoresis and an apparatus to be used for working the method.

The method of this invention comprises superposing a plurality of reaction membranes each having a different species of antibody or antigen supported on an electrophoretic carrier, inserting the resulting laminate in an electrolyte, adding to the electrolyte those antigens or antibodies which correspond to the plurality of antibodies or antigens supported on the aforementioned reaction membranes, immobilizing the added antigens or antibodies by their being electrophoretically moved and allowed to react with the corresponding reactive antibodies or antigens supported on the reaction membranes, adding a plurality of labeled antibodies or antigens further to the electrolyte, electrophoretically moving the added labeled antibodies or antigens and allowing them to react with the aforementioned immobilized antigens or antibodies or with the antibodies or antigens supported in the unreacted form on the reaction membranes thereby immobilizing the labeled antibodies or antigens, and measuring the concentration of the labeled antibody or antigen on each of the reaction membranes. To be more specific, this invention permits the concentration of a given plurality of antigens or antibodies to be measured simultaneously and quickly by supporting the plurality of antibodies or antigens each on electrophoretic carriers thereby preparing reaction membranes, superposing the reaction membranes, placing the resulting laminate in an electrolyte, adding to the electrolyte a plurality of antigens or antibodies, immobilizing the added antigens or antibodies by their being electrophoretically moved and allowed to react with the corresponding antibodies or antigens supported on the reaction membranes, further adding to the electrolyte labeled antibodies or antigens, electrophoretically moving the labeled antibodies or antigens and allowing them to react with the antibodies or antigens already immobilized through reaction or with the immobilized yet unreacted antibodies or antigens, and measuring the concentrations of the labeled antibodies or antigens.

The measurement of a plurality of different tumor markers by the use of this invention, therefore, can be attained by an expeditious procedure using only a small amount of sample liquid.

In this measurement, the antibodies or antigens to be used for the measurement may be selected on condition that they will produce plural specific antigen-antibody reactions.

The other objects and characteristics of this invention will become apparent from the description given in further detail hereinbelow with reference to the accompanying drawings.

DETAILED DESCRIPTION OF THE PREFERRED EMBODIMENTS

Figure 1A:
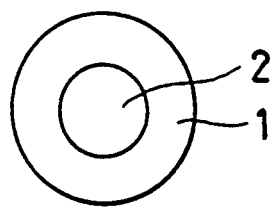
FIG. 1(a) is a front view of a reaction membrane to be used in working the present invention.

The method of this invention for effecting the determination by means of antigen-antibody reactions comprises (a) a step of forming a plurality of different reaction membranes each having a different antibody or antigen supported on an electrophoretic carrier, superposing these reaction membranes, and inserting the resulting laminate in an electrolyte, (b) a step of adding to the electrolyte a plurality of antigens or antibodies corresponding to the plurality of different species of antibodies or antigens supported on the aforementioned reaction membranes and immobilizing the added antigens or antibodies by electrophoretically moving them through the electrolyte and enabling them to react with the antibodies or antigens supported on the reaction membranes, (c) a step of adding a plurality of different species of labeled antibodies or antigens to the electrolyte and immobilizing the labeled antibodies or antigens by their being electrophoretically moved through the electrolyte and allowed to react with the aforementioned immobilized antigens or antibodies or with the antibodies or antigens retained in an unreacted form on the reaction membranes, and (d) a step of measuring the concentrations of the immobilized labeled antibodies or antigens one for each of the reaction membranes.

The antibodies or antigens to be used in the measurement contemplated by this invention may be selected on condition that they will severally produce specific antigen-antibody reactions.

For example, AFP ($\alpha$-fetoprotein), $\beta_2$-microglobulin, CEA (carcinoembryonic antigen), etc. are usable as antigens.

As electrophoretic carriers, polyacrylamide gel, agarose gel, etc. can be used.

The formation of a reaction membrane having an antibody or antigen supported on an electrophoretic carrier can be effected, for example, by a procedure which comprises adding an antibody or antigen and a polymerizing agent to a solution of acrylamide or agarose thereby preparing a polymerization liquid and gelling this polymerization liquid within a ring made of glass, quartz, or polystyrene.

As electrolytes, buffers such as of tris(hydroxymethyl)aminomethane and glycine can be used.

As labels, fluorescent pigments such as, for example, fluorescein isothiocyanate (FITC) and rhodamine isothiocyanate (RITC) can be used. Such a fluorescent pigment is bound to a given antibody or antigen by the Goldman method (as taught in "Fluorescent Antibody Method": New York, 1968, Academy Press), with necessary modifications.

The apparatus of this invention for determining the concentrations of antigens or antibodies by means of electrophoresis is so constructed as to permit insertion in an electrolyte of a laminate which is obtained by forming a plurality of reaction membranes each having a different species of antigen or antibody supported on an electrophoretic carrier and superposing the plurality of reaction membranes. In accordance with the present invention, one item or a plurality of items of immunoassay can be easily and quickly carried out. Thus, the apparatus for determination of the present invention can be utilized as an apparatus for multiple-item immunoassay, as an apparatus for the measurement of tumor markers, and as an apparatus for the immunological diagnosis of cancerous growths.

There are times when the sample liquids subjected to determination contain large molecules having molecular weights of some hundreds of thousands and precipitates in addition to antigens or antibodies subjected to determination and such extraneous substances are possibly caught on the surfaces of electrophoretic carriers in the apparatus so as to jeopardize the accuracy of determination.

In this case, the adverse effects exerted by such extraneous substances as large molecules and precipitates can be eliminated and the accuracy of determination can be ensured by superposing a freely detachable filter on the upper surface of one reaction membrane to be inserted as carrying an antibody or antigen thereon into an electrolytic cell for electrophoresis or on the upper surface of the uppermost one of a plurality of reaction membranes inserted in a superposed form into the electrolytic cell.

As the filter, an electrophoretic carrier having no antigen or antibody supported thereon or a web of glass fibers may be used.

The movement of an antibody or antigen in the electrolyte has been described as effected by means of electrophoresis. By suitably selecting the material for the reaction membrane, however, the movement of the antibody or antigen indispensable to the effective determination of the concentration of the antigen or antibody may be attained without any recourse to electrophoresis.

In short, the present invention permits the determination of concentrations of a plurality of antigens or antibodies to be effected simultaneously and quickly. For example, it enables the measurement of a plurality of different tumor markers to be effected by an expeditious procedure using only a small amount of sample liquid. In the present invention, the amount of sample liquid used for the determination does not depend upon the number of items of determination. The amount of sample liquid required per item of determination is inversely proportional to the number of items of determination simultaneously performed, i.e. the amount of sample liquid decreases in proportion as the number of items of determination increases. Where the determination is to be made on five components, for example, the amount of sample liquid required is about one fifth of the amount required for the determination by the conventional method.

The filter superposed on the reaction membrane having an antibody or antigen supported thereon serves to keep large molecules and precipitates out of the sample liquid and, therefore, improves the accuracy of determination to as much as about twice the level attainable without the use of the filter.

Now, the present invention will be described more specifically below with reference to working examples. It should be noted that the present invention is not limited to these examples.

EXAMPLE 1:

An annularly molded glass plate was subjected to a silane coupling treatment as follows. In 25 ml of ethanol, 75 µl of methacrylic acid-3-trimethoxysilyl-propyl ester and 750 µl of an aqueous 10% acetic acid solution were stirred. In the resultant mixture, the glass ring was immersed for several minutes. The glass ring was removed from the liquid mixture, dried once, and then cleaned with ethanol. It was then maintained at 110° C. for one hour.

As an electrophoretic carrier, polyacrylamide was used. Reaction membranes each having a different species of antibody supported on the carrier were produced as follows. In an ice-cooled atmosphere, 0.5 ml of a specific species of antibody (about 5 mg/ml) and 25 ml of an aqueous 0.25% acrolein solution were left to react with each other for 30 minutes. Then, the resulting reaction mixture was thoroughly dialyzed with phosphate buffer. A polymerization liquid was obtained by stirring the resulting dialysate with 1.5 ml of an aqueous 0.32 g/ml acrylamide solution, 1.5 ml of an aqueous 0.016 g/ml N,N'-methylenebisacrylamide solution, 1.25 ml of an aqueous 4.6 µl/ml N,N,N',N'-tetramethylethylene diamine solution and 5.75 ml of an aqueous 1.2 mg/ml ammonium persulfate solution.

The glass ring resulting from the aforementioned silane coupling treatment was mounted on an acrylic resin plate, the polymerization liquid was quickly dropped onto the glass ring, and another acrylic resin plate was placed on top of the glass ring so as to sandwich the glass ring between the two acrylic resin plates. This work was carried out carefully so as to avoid entrapping bubbles in the polymerization liquid. The laminate thus formed was left standing until the polymerization liquid gelled. Then, the acrylic resin plates were removed. Consequently, inside the glass ring, a gelled membrane of polyacrylamide having the antibody chemically bound therein was formed as joined integrally with the glass ring. Other reaction membranes similarly incorporating other species of antibodies were prepared by repeating the procedure. In this case, the glass rings were desirably given a thickness of not more than 3 mm.

Figure 1B:
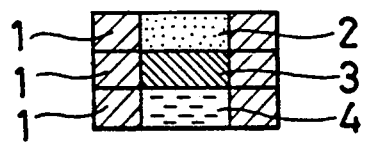
FIG. 1(b) is a longitudinally sectioned side view of the reaction membrane of FIG. 1(a).
Figure 2:
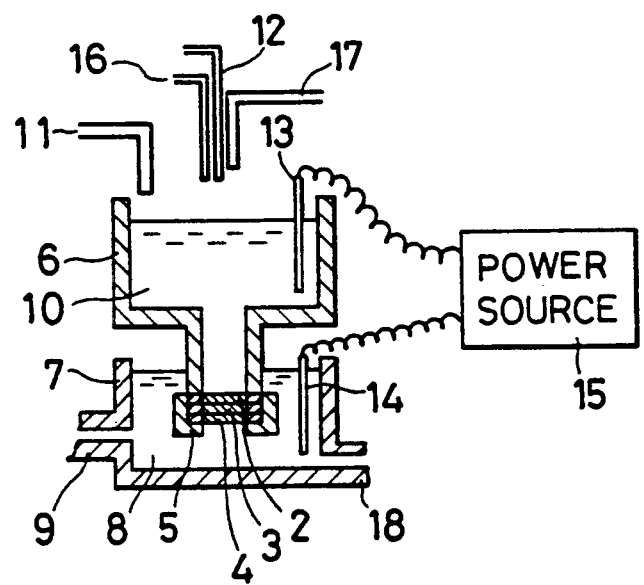
FIG. 2 is a schematic diagram illustrating a typical apparatus for measuring the concentration of an antigen.
Figure 3:
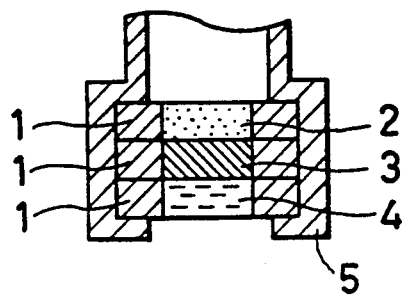
FIG. 3 is a magnified view illustrating the reaction membrane of FIG. 1 as set in place in the apparatus of FIG. 2.

Now, the procedure of the determination will be described below with reference to FIG. 2. The reaction membranes 2, 3, and 4 prepared in the manner described above and joined integrally with the glass rings 1 where superposed as shown in FIG. 1. The reaction membranes 2, 3, and 4 with the glass rings 1, thus piled up were fitted in the bottom part of an upper electrolytic cell 6 with the aid of a reaction membrane retainer 5 made of acrylic resin. A lower electrolytic cell 7 was filled with an electrolyte 8 which was introduced via an electrolyte inlet 9. Then, the upper electrolytic cell 6 was filled with an electrolyte 10 which was introduced via an electrolyte injection nozzle 11. A sample liquid was added to sucrose in an amount calculated to give rise to a 15% sucrose solution. A 10-µl portion of the sample solution was gently poured onto the reaction membrane via a sample injection nozzle 12. Meanwhile, the leading end of the sample injection nozzle 12 was moved to the neighborhood of the reaction membrane.

A voltage was applied with a DC power source 15 in such a manner that an electrode 13 would function as a cathode and an electrode 14 as an anode. The magnitude of this voltage was 100 V and the duration of the application of the voltage was 30 minutes.

Then, an FITC-bound antibody prepared by following the Goldman method with necessary modifications was dissolved in sucrose added thereto in an amount calculated to give rise to a 15% sucrose solution. A 20-µl portion of the resulting antibody solution was gently poured onto the reaction membrane via a labeled antibody injection nozzle 16. Similarly to the sample solution, this antibody solution was subjected to application of voltage. The magnitude of the voltage applied this time was 100 V and the duration of the application of this voltage was 30 minutes. The FITC-bound antibody may be obtained by effecting the labeling after the antibody is mixed with an antibody corresponding to the specific species of antigen mentioned above. Otherwise, it may be obtained by effecting the mixing after the labeling is made. During the injection of the labeled antibody, the leading end of the labeled antibody injection nozzle 16 is desired to be moved to the neighborhood of the reaction membrane 2.

The electrolyte in the upper electrolytic cell and that in the lower electrolytic cell were removed by means of an electrolytic discharge nozzle 17 and an electrolyte discharge outlet 18. Subsequently, a $10^{-2}M$ phosphate buffer was poured in via the electrolyte injection nozzle and the electrolyte injection inlet to wash the reaction membrane. Thereafter, the resulting washings were discharged via the electrolyte discharge nozzle and the electrolyte discharge outlet.

The reaction membranes were removed and were each tested for the amount of residual FITC through fluorescent measurement. The excitation wavelength was 480 nm and the fluorescent wavelength was 525 nm.

Figure 4A:
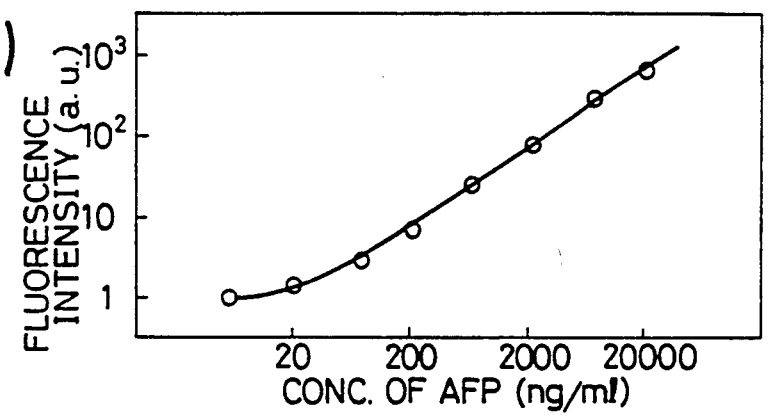
FIGS. 4(a), 4(b) and 4(c) are calibration curves obtained in the working examples of this invention on antigens used for the measurement.
Figure 4B:
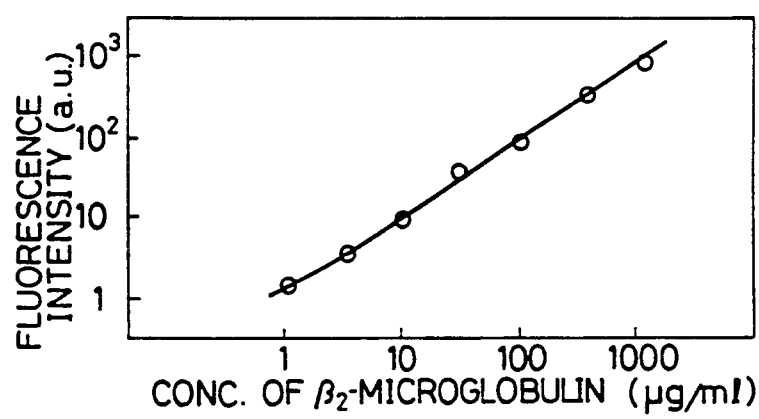
Figure 4C:
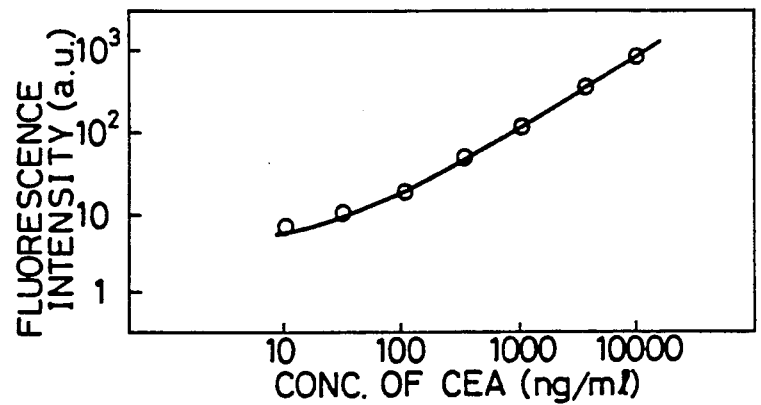

As antigens subjected to determination, AFP (α-fetoprotein), $\beta_2$-microglobulin, and CEA (carcinoembryonic antigen) were used. Samples containing these antigens in varying concentrations were prepared and subjected to the determination by following the procedure mentioned above, to obtain calibration curves. The results were as shown in FIG. 4. FIG. 4(a) represents a calibration curve obtained for the AFP concentration, FIG. 4(b) a calibration curve obtained for the $\beta_2$-microglobulin concentration, and FIG. 4(c) a calibration curve obtained for the CEA concentration. These results agree satisfactorily with those obtained respectively by the conventional method. The coefficients of correlation were 1.02 for the AFP, 0.95 for the $\beta_2$-microglobulin, and 0.97 for the CEA respectively.

These results indicate that the method of the present invention permits a plurality of items of determination to be simultaneously effected.

The labels used for the labeled antibodies may be either different from one another or similar to one another.

The determination of the amount of an antigen immobilized on the reaction membrane may be effected by a procedure which comprises causing a labeled antigen to react with a chemically bound and yet unreacted antibody and measuring the concentration of the product of this reaction.

EXAMPLE 2

A glass ring 1 was treated similarly to that of Example 1. A reaction membrane 19 was prepared by adding 25 μl of an aqueous 0.25% acrolein solution to 0.5 ml of 1 g G fraction (5 mg/ml) of antiserum against human-alpha fetoprotein (AFP) and treating the resulting mixture in the same manner as in Example 1.

An electrophoretic carrier containing no antibody was used as a filter. This electrophoretic carrier containing no antibody was joined to the glass ring by using 0.5 ml of a $10^{-2}$M phosphate buffer (pH 7.2) in place of the antibody resulting from reaction with acrolein in the same manner as in Example 1.

Figure 5A:
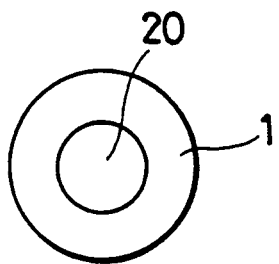
FIG. 5(a) is a front view of a reaction membrane provided on the upper side thereof with a filter, as another embodiment of the present invention.
Figure 5B:
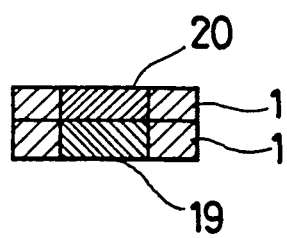
FIG. 5(b) is a longitudinally sectioned side view of the reaction membrane of FIG. 5(a).
Figure 6:
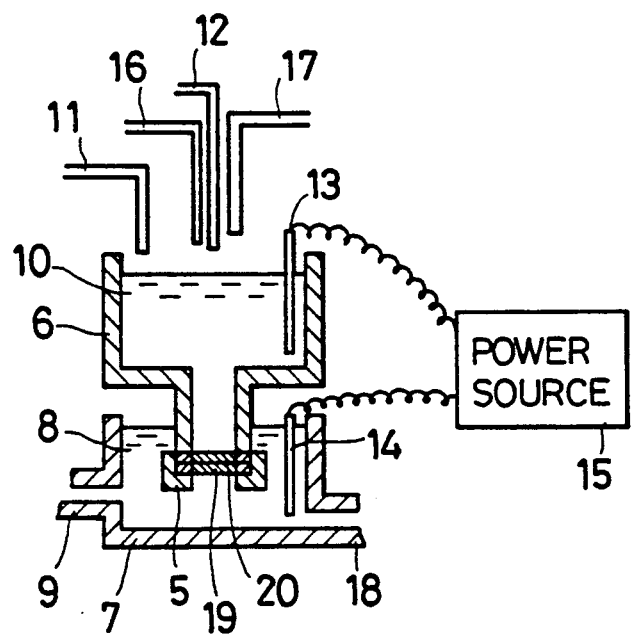
FIG. 6 is a schematic diagram illustrating another typical apparatus for measuring the concentration of an antigen.

The filter 20 produced as described above was superposed on the reaction membrane 19 as illustrated in FIG. 5. The combination of the filter and the reaction membrane was set in the bottom part of an upper electrolytic cell 6 with the aid of a reaction membrane retainer 5 of a concentration tester illustrated in FIG. 6. A lower electrolytic cell 7 was filled with an electrolyte 8 which was introduced via an electrolyte inlet 9. Then, the upper electrolytic cell 6 was filled with an electrolyte 8 which was introduced via an electrolyte injection nozzle 11. A sample liquid was added to sucrose in an amount calculated to give rise to a 15% sucrose solution. Subsequently, the leading end of a sample solution injection nozzle 12 was moved to the neighborhood of the filter 20 and 20 μl of the sample solution was gently poured onto the electrophoretic carrier via the nozzle 12.

A voltage was applied with a DC power source 15 in such a way that an electrode 13 would function as a cathode and an electrode 14 as an anode respectively. The magnitude of the voltage thus applied was 50 V and the duration of the voltage application was 20 minutes.

Then, an FITC-bound antibody prepared by following the Goldman method with necessary modifications was added to sucrose in an amount calculated to give rise to a 15% sucrose solution. A 20 μl portion of the resulting solution was gently poured onto the filter 20 via a labeled antibody injection nozzle 16 and was subjected to application of voltage similarly to the sample solution. The magnitude of the voltage thus applied was 50 V and the duration of voltage application was 20 minutes.

The electrolyte in the upper electrolytic cell and that in the lower electrolytic cell were discharged via an electrolyte discharge nozzle 17 and an electrolyte discharge outlet 18. Then, the reaction membrane 19 was removed in conjunction with the glass ring 1 and rinsed in a $10^{-2}$M phosphate buffer.

Figure 7:
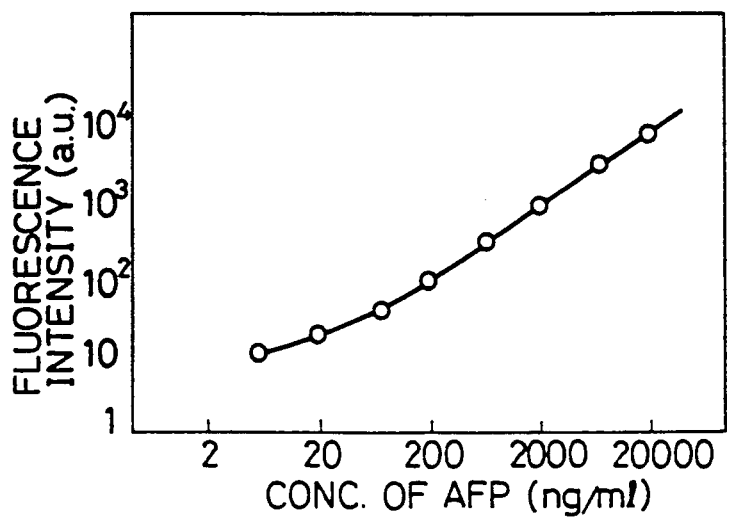
FIG. 7 is a calibration curve obtained by the use of the reaction membrane of FIG. 5(a) on an antigen used for the measurement.

The reaction membrane was tested for the amount of immobilized FITC in terms of intensity of fluorescence. The exciting wavelength was 485 nm and the fluorescent wavelength was 520 nm. AFP samples of different concentrations were tested by the procedure mentioned above to obtain a calibration curve. The results were as shown in FIG. 7. The determination performed on the standard AFP sample of a concentration of 20 ng/ml produced results indicating the average to be 19.8 ng/ml and the standard error to be 3.0 ng/ml.

Separately, the determination was performed by the conventional method using only the reaction membrane without passing the sample solution or the labeled antibody through a filter. In this case, the determination similarly performed on the standard AFP sample of a concentration of 20 ng/ml produced results indicating the average to be 19.5 ng/ml and the standard error to be 5.5 ng/ml.

The results clearly indicate that the filter mounted on the reaction membrane was effective in removing large molecules and precipitates from the sample solution and the labeled antibody and consequently improving the accuracy of determination to a notable extent.

Where the sample liquid to be subjected to determination happens to contain precipitates or large molecules in a large amount, it is desirable to prepare separate filters and use them severally in the step of electrophoretically moving the sample for reaction and the step of electrophoretically moving the labeled antibody for reaction.

What is claimed is:

1. A method for the determination of the species of antigens or antibodies contained in a sample liquid effected by immobilizing said antigens or antibodies in a reaction membrane by allowing said antigens or antibodies to react with antibodies or antigens chemically bound in said reaction membrane, which are specific to said antigens or antibodies contained in added sample liquid, and measuring the concentration of said antigens or antibodies immobilized in said membrane, said method comprising the steps of:

(i) preparing a plurality of reaction membranes each having one of a plurality of species of antibodies or antigens chemically bound to the gelled electrophoretic carrier of a membrane;

(ii) superposing said reaction membrane into a laminate and inserting said laminate in an electrolyte so as to partition said electrolyte into an upper electrolyte and a lower electrolyte;

(iii) adding said sample liquid to said upper electrolyte;

(iv) electrophoretically moving antigens or antibodies contained in said added sample liquid toward said lower electrolyte and allowing said antigens or antibodies to react with said antibodies or antigens bound in said reaction membranes which are specific to said antigens or antibodies contained in said added sample liquid, thereby immobilizing the added antigens or antibodies in at least one of said membranes;

(v) adding to said upper electrolyte a plurality of species of labeled antibodies or labeled antigens, each having the same specificity as that of each species of said antibodies or antigens bound in said reaction membranes;

(vi) electrophoretically moving said labeled antibodies or labeled antigens toward said lower electrolyte to react with said antigens or antibodies contained in said added sample liquid and then immobilized in said reaction membranes, thereby immobilizing the labeled antibodies or labeled antigens in said reaction membranes;

(vii) separating said laminated reaction membranes; and (viii) measuring the concentrations of the labeled antibodies or labeled antigens immobilized on each of said separated reaction membranes.

2. The method according to claim 1, wherein at least one of said reaction membranes has antibodies of a species specific to an antigen which is a tumor marker.

3. The method according to claim 1, further comprising the step of placing said plurality of reaction membranes within glass rings, said placing step being carried out between the steps (i) and (ii).

4. The method according to claim 1, further comprising the step of superposing a filter made of a material which is the same as that of said electrophoretic carrier on the uppermost one of said reaction membranes of said laminate and said filter material being a material which prohibits large molecules having molecular weights of hundreds of thousands to pass therethrough, said step being carried out before inserting said laminate in said electrolyte in the step (ii).

5. An apparatus for use in the determination of the species of antigens or antibodies contained in a sample liquid effected by immobilizing said antigens or antibodies in a reaction membrane by allowing said antigens or antibodies to react with antibodies or antigens chemically bound in said reaction membrane, which are specific to said antigens or antibodies contained in said sample liquid, and immobilizing labeled antibodies or labeled antigens of a species which have the same specificity as that of said antibodies or antigens bound in said reaction membrane by allowing said labeled antigens or labeled antibodies to react with said antibodies or antigens immobilized in said reaction membrane, said apparatus comprising:

an electrolyte cell having an upper cell and a lower cell each provided with an electrode contacting an electrolyte therein;

a laminate of a plurality of reaction membranes each comprised of a gelled electrophoretic carrier and an antibody or antigen of a plurality of such species chemically bound to said gelled electrophoretic carrier, each being specific to each species of antigens or antibodies which may be contained in said sample liquid;

means for retaining said laminate in said electrolyte cell at the bottom of said upper cell;

means for adding said sample liquid to said upper cell;

means for adding labeled antibodies or labeled antigens of a plurality of species to said upper cell, each having the same specificity as that of each of said antibodies or antigens chemically bound in said membranes;

a voltage source means for supplying an electrophoretic voltage between said electrodes when said sample liquid is added so that said voltage causes said antigens or antibodies contained in added sample liquid to electrophoretically move toward said lower cell and to react with said chemically bound antibodies or antigens which are specific to said moving antigens or antibodies, thereby immobilizing said antigens or antibodies in at least one of said membranes, and supplying again said voltage when said labeled antigens or labeled antibodies are added so that said voltage causes said labeled antigens or labeled antibodies to electrophoretically move toward said lower cell and causes labeled antigens or labeled antibodies of at least one species specific to antigens or antibodies contained in said sample liquid to react with said antibodies or antigens immobilized in at least one of said membranes; and said laminated reaction membranes being operable from one another in order to be able to measure the concentrations of the labeled antibodies or antigens immobilized on each of said separated reaction membranes.

6. The apparatus according to claim 5, wherein at least one of said reaction membranes has antibodies of a species specific to an antigen which is a tumor marker.

7. The apparatus according to claim 5, further comprising a plurality of glass rings each containing one of said plurality of reaction membranes therewithin.

8. An apparatus for use in the determination of the species of antigens or antibodies contained in a sample liquid effected by immobilizing said antigens or antibodies in a reaction membrane by allowing said antigens or antibodies to react with antibodies or antigens chemically bound in said reaction membrane, which are specific to said antigens or antibodies contained in said sample liquid, and immobilizing labeled antibodies or labeled antigens of a species which have the same specificity as that of said antibodies or antigens bound in said reaction membrane by allowing said labeled antigens or labeled antibodies to react with said antibodies or antigens immobilized in said reaction membrane, said apparatus comprising:

an electrolyte cell having an upper cell and a lower cell each provided with an electrode contacting an electrolyte therein;

a laminate at a plurality of reaction membranes each comprising a gelled electrophoretic carrier and an antibody or antigen of a plurality of such species chemically bound to said electrophoretic carrier, each being specific to each species of antigens or antibodies which may be contained in said sample liquid;

a filter superposed on said laminate for prohibiting large molecules having molecular weights of hundreds of thousands to pass therethrough and made of a material which is the same as that of said electrophoretic carrier;

means for retaining said laminate and said filter in said electrolyte cell at the bottom of said upper cell;

means for adding said sample liquid to said upper cell;

means for adding labeled antibodies or labeled antigens of a plurality of species, each having the same specificity as that of each of said antibodies or antigens chemically bound in said membranes; and a voltage source means for supplying an electrophoretic voltage between said electrodes when said sample liquid is added so that said electrophoretic voltage causes said antigens or antibodies contained in added sample liquid to electrophoretically move toward said lower cell and to react with said chemically bound antibodies or antigens which are specific to said moving antigens or antibodies, thereby immobilizing said antigens or antibodies in said membranes, and supplying again said voltage when said labeled antigens or labeled antibodies are added so that said electrophoretic voltage causes said labeled antigens or labeled antibodies to electrophoretically move toward said lower cell and to react with said antibodies or antigens immobilized in said membranes.

9. The apparatus according to claim 8, wherein at least one of said reaction membranes has an antibody specific to an antigen which is a tumor marker.

10. The apparatus according to claim 8, wherein said filter is a glass fiber.

11. The apparatus according to claim 8, further comprising a plurality of glass rings each containing one of said plurality of reaction membranes therewithin.

* * * * *